(12) United States Patent
Pahnke

(10) Patent No.: US 9,370,523 B2
(45) Date of Patent: Jun. 21, 2016

(54) METHOD FOR DIAGNOSING OR PREDIAGNOSING A BETA-AMYLOIDOPATHY OR AN ALPHA-SYNUCLEOPATHY

(71) Applicant: Immungenetics AG, Rostock (DE)

(72) Inventor: Jens Pahnke, Rostock (DE)

(73) Assignee: Immungenetics AG, Rostock (DE)

( * ) Notice: Subject to any disclaimer, the term of this patent is extended or adjusted under 35 U.S.C. 154(b) by 31 days.

(21) Appl. No.: 14/499,918

(22) Filed: Sep. 29, 2014

(65) Prior Publication Data

US 2015/0024418 A1 Jan. 22, 2015

Related U.S. Application Data

(62) Division of application No. 13/821,515, filed as application No. PCT/EP2011/064893 on Aug. 30, 2011.

(30) Foreign Application Priority Data

Sep. 7, 2010 (DE) .................. 10 2010 044 561

(51) Int. Cl.
*G01N 33/68* (2006.01)
*A61K 31/5415* (2006.01)
*C07D 279/24* (2006.01)
*C07D 417/06* (2006.01)
*C07D 417/14* (2006.01)
*A61K 31/495* (2006.01)
*C07D 279/28* (2006.01)
*G01N 33/48* (2006.01)

(52) U.S. Cl.
CPC ........... *A61K 31/5415* (2013.01); *A61K 31/495* (2013.01); *C07D 279/24* (2013.01); *C07D 279/28* (2013.01); *C07D 417/06* (2013.01); *C07D 417/14* (2013.01); *G01N 33/48* (2013.01); *G01N 33/6896* (2013.01); *G01N 2333/705* (2013.01); *G01N 2800/2814* (2013.01); *G01N 2800/2821* (2013.01); *G01N 2800/2835* (2013.01)

(58) Field of Classification Search
None
See application file for complete search history.

(56) References Cited

FOREIGN PATENT DOCUMENTS

WO WO-96/04915 A1 2/1996
WO WO-2008/092898 A1 8/2008

OTHER PUBLICATIONS

International Search Report and Written Opinion for Application No. PCT/EP2011/064893, dated Jul. 5, 2012.
International Preliminary Report on Patentability for Application No. PCT/EP2011/064893, dated Mar. 12, 2013.
Cirrito et al., "P-glycoprotein Deficiency at the Blood-Brain Barrier Increases Amyloid-Beta Deposition in an Alzheimer Disease Mouse Model," *Journal of Clinical Investigation*, 115(11):3285-3290 (2005).
Pahnke et al., "Clinico-Pathologic-Function of Cerebral ABC Transporters-Implications for the Pathogenesis of Alzheimer's Disease," *Current Alzheimer Research*, 5(4):396-405 (2008).
Deeley et al., "Substrate Recognition and Transport by Multidrug Resistance Protein 1 (ABCC1)," *FEBS Letters*, 580(4):1103-1111 (2006).
Krohn et al., "Cerebral Amyloid-β Proteostasis is Regulated by the Membrane Transport Protein ABCC1 in Mice," *Journal of Clinical Investigation*, 121(10):3924-3931 (2011).
Tao et al., "Cediranib (recentin, AZD2171) Reverses ABCB1- and ABCC1-Mediated Multidrug Resistance by Inhibition of Their Transport Function," *Cancer Chemotherapy and Pharmacology*, 64(5):961-966 (2009).
Kortekaas et al., "Blood-Brain Barrier Dysfunction in Parkinsonian Midbrain in vitro," Ann Neurol, 57:176-179 (2005).
Coisne et al., "Mouse Syngenic in vitro Blood-Brain Barrier Model: A New Tool to Examine Inflammatory Events in Cerebral Endothelium," *Laboratory Investigation*, 85:734-746 (2005).

*Primary Examiner* — Theodore R West
(74) *Attorney, Agent, or Firm* — Marshall, Gerstein & Borun LLP

(57) ABSTRACT

The invention relates to a method for the diagnosis or prediagnosis of a β-amyloidopathy or an α-synucleopathy accompanied by a cerebral protein deposit and a reduced activity of the cerebral ABCC1-transporter, or for determining the risk of a proband suffering from such an illness, the proband already having accumulated substances transported by the cerebral ABCC1 transporter.

5 Claims, 12 Drawing Sheets

METHOD FOR DIAGNOSING OR PREDIAGNOSING A BETA-AMYLOIDOPATHY OR AN ALPHA-SYNUCLEOPATHY

CROSS-REFERENCE TO RELATED APPLICATIONS

This is a division of U.S. patent application Ser. No. 13/821,515, which is the U.S. national phase of PCT/EP2011/064893 filed Aug. 30, 2011, which claims the Convention priority of DE 10 2010 044 561.4 filed Sep. 7, 2010, the respective entire disclosures of which are incorporated herein by reference.

BACKGROUND OF THE INVENTION

The accumulation of proteins or protein fragments (peptides) in the brain is a significant feature of age-dependent neurodegenerative diseases. In Alzheimer's dementia (Alzheimer's disease, AD) and cerebral β-amyloidopathy (CAA) the aggregation of β-amyloid peptides (Aβ) is a trigger factor, the basic mechanism being unknown. The AR proteostasis, i.e. the equilibrium of production and degradation/removal by means of receptors or proteases is disturbed in AD and CAA. However, so far little attention has been paid to the removal of Aβ peptides by cellular transporters (ABC transporters). In Parkinson's disease, the protein α-synuclein accumulates, which inter alia regulates the dopamine release in the substantia nigra. In Parkinson's disease α-synucleinopathy it is known that ABC transporters play a crucial role for transport (Kortekaas et al., Ann Neural 2005, 57, 176-179). Here there are several subfamilies A-G which can alternatingly transport various substrates (metabolites, medicaments, peptides, proteins, ions) and are even able to replace each other in the transport function (e.g. ABCB1 and ABCC1, Tao et al. Cancer Chemotherapy and Pharmacology, 64, 5, 961-969).

It has been shown by means of various genetically modified mouse models that the ABC transporter (a common structural element of the ABC transporter is an ATP-binding cassette and a transport pore) ABCC1 is an important protein/peptide transporter, in particular Aβ transporter, which has extraordinary functional effects on the cerebral protein accumulation. ABCC1 is also an important α-synuclein transporter.

The investigations of the transporter activity are shown as an example hereinafter for Aβ transport.

In order to determine the ABCC1 activity in vivo, in APP-expressing, transgenic mice, the ABCB1, ABCG2 or ABCC1 transporter was removed genetically (knockout mice) in each case.

Here it was found that:
i) the quantity of Aβ in the mice lacking the ABCC1 transporter was increased by a factor of 12,
ii) loss of the ABCB1 transporter only results in a threefold increase and
iii) loss of ABCG2 has no Aβ-accumulating effect.

DESCRIPTION OF THE INVENTION

Accordingly, the invention provides substances which suitably influence the ABCC1 transporter in order to thus be able to treat neurodegenerative diseases, in particular β-amyloidopathies or α-synucleopathies. Specifically, the invention provides 2-($R^2$-thio)-10-[3-(4-$R^1$-piperazin-1-yl)propyl]-10H-phenothiazines.

In other words, the object was solved by 2-($R^2$-thio)-10-[3-(4-$R^1$-piperazin-1-yl)propyl]-10H-phenothiazines according to the general formula I

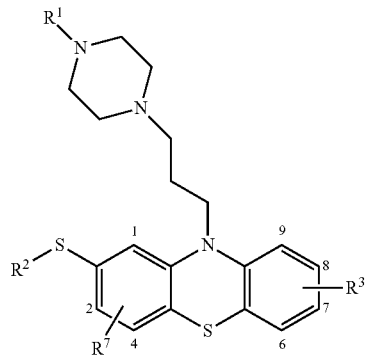

wherein the residues
$R^1$ and $R^2$ are the same or different and each independently of one another are $C_1$-$C_6$ alkyl groups, which independently of one another optionally comprise another substituent selected from alkyl, aryl, acyl (preferably acetyl), amino, nitro, sulfonyl, hydroxyl, alkoxy, aryloxy, arylthio, alkylthio groups and halogen atoms, wherein the respective alkyl groups optionally comprise at least one further halogen atom and the residue
$R^3$ is located at one of the positions 6-9 of the phenothiazine ring system and is a hydrogen atom or an alkyl, aryl, acyl (preferably acetyl), amino, nitro, sulfonyl, hydroxyl, alkoxy, aryloxy, arylthio or alkylthio group or a halogen atom, wherein the respective alkyl groups optionally comprise at least one further halogen atom or an $NR^4R^5$ or $OR^6$ group, wherein $R^4$, $R^5$ and $R^6$ are the same or different and each independently of one another are selected from hydrogen and $C_1$-$C_3$ alkyl groups and the residue
$R^7$ is located at one of the positions 1, 2 or 4 of the phenothiazine ring system and is a hydrogen atom or an alkyl, aryl, acyl (preferably acetyl), amino, nitro, sulfonyl, hydroxyl, alkoxy, aryloxy, arylthio or alkylthio group or a halogen atom, wherein the respective alkyl groups optionally comprise at least one further halogen atom or an $NR^8R^9$ or $OR^{10}$ group, wherein $R^8$, $R^9$ and $R^{13}$ are the same or different and each independently of one another are selected from hydrogen and $C_1$-$C_3$ alkyl group, for treating a β-amyloidopathy or an α-synucleinopathy accompanied by a cerebral protein deposit.

Furthermore, both in the case of α-synucleinopathies and in the case of β-amyloidopathies, there is a need to identify or to diagnose or prediagnose these diseases.

The invention also provides a method with which α-synucleinopathies and also β-amyloidopathies can be diagnosed or prediagnosed. Specifically, the invention provides a method for the diagnosis or prediagnosis of a β-amyloidopathy or α-synucleopathy or for determining the risk of a proband to develop such an illness, wherein the proband already takes substances transported by the cerebral ABCC1 transporter, including the following steps:
a) determining the quantity of ingested substance in body fluid samples of the proband at a specific time point;
b) repeating the determination of step a) at at least one further later time point;
c) comparing the quantities determined in step a) and b) with quantities which had been defined as characteristic at the same time points for probands who at the time of the sampling showed no clinical symptoms of a β-amyloidopathy or an α-synucleopathy.

The fact that the proband already takes at least one substance which is transported via the cerebral ABCC1 transporter means that this substance needs not to be administered. On the contrary it is already present in the body of the proband, for example, as a result of a drug treatment of another disease. The body fluid samples of the proband which are studied are preferably samples from blood plasma, blood serum and/or cerebral spinal fluid.

The β-amyloidopathy is preferably an Alzheimer's dementia, the α-synucleinopathy is preferably Parkinson's disease. Optionally, the α-synucleinopathy can also be a dementia with Lewy bodies (DLB). Substances which are transported via the cerebral ABCC1 transporter are preferably selected from antibiotics (e.g. difloxacin, grepafloxacin), virostatics/antiviral medicaments (e.g.saquinavir, ritonavir), anti-allergics/antihistamines (e.g.cimetidine), cardio-vascular medicaments (e.g. verapamil), antidepressants (e.g. citalopram), antihyperuricemics (e.g. probenecid), cytostatics (e.g. methotrexate, etoposit, edatrexate, ZD1694), vitamins/vitaminanalogues (e.g. methotrexate, folic acid, L-leucovorin), antiphlogistics (e.g. indomethacin), anti-epileptics (e.g. valproic acid), hormones/hormone derivatives (e.g. 17β-estradiol), leukotrienes (e.g. LTC4), fluorescent samples (e.g. calcein, Fluo-3, BCECF, SNARF), GSH-, sulphateorglucuronide-coupledmetabolites of natural substances (endogenously produced), toxinsor of medicaments (e.g. 2,4-dinitrophenyl-SG, bimane-SG, N-ethylmaleimide-SG, doxorubicin-SG, thiotepa-SG, cyclophosphamide-SG, melphalan-SG, chlorambucil-SG, ethacrynic acid-SG, metolachlor-SG, atrazine-SG, sulforaphan-SG, aflatoxin B1-epoxide-SG, 4-nitroquinolin 1-oxide-SG, As(SG)3, etoposide-gluc, 4-(methylnitrosamino)-1-(3-pyridyl)-1-butanol (NNAL)-3β-O-gluc, SN-38-gluc, 4-methylumbelliferyl-β-d-gluc, 6-hydroxy-5,7-dimethyl-2-methylamino-4-(3-pyridylmethyl)-benzothiazolsulfate (E3040S)-gluc, leukotriene C4, prostaglandin A2-SG, 15-deoxy-Δ12,14 prostaglandin J2-SG, hydroxynonenal-SG, 17β-estradiol-17-β-d-gluc, glucuronosylbilirubin, bis-lucuronosylbilirubin, hyodeoxycholate-6-α-gluc, estron-3-sulfate, dehydroepiandrosteronesulfate, sulfatolithocholate) (see also Deeley R G et al.: Substrate recognition and transport by multi drug resistance protein 1 (ABCC1), FEBS letters 2006, 580 (4), pp. 1103-1111.)

This indirect analysis of the transport activity of ABCC1 transporters can be used for the diagnosis/prediagnosis of a corresponding disease. In probands who already take ABCC1-transportable substances by other routes, the profile of the active substance concentration in body fluids, preferably blood plasma, serum and/or cerebrospinal fluid can be investigated. A time-dependentmeasurement for probands in whom there is a reduced ABCC1 transport activity compared with healthy probands shows a delayed or shifted substance concentration curve (concentration c plotted over time t), i.e. the maximum of the curve varies with time.

When a shifted curve is obtained compared with the healthy case, this is an indication of a changed ABCC1 transport activity. This means that substances such as Aβ or α-synuclein are transported less efficiently and is therefore an indication of a corresponding disease.

Both the mouse model and the pharmacological influencing of the ABCC1 show that this is an important cellular transmembrane transporter for the Aβ protein and imply that the blood-brain barrier and the plexus choroideus occupy a key position for the Aβ release from the brain. It could be shown that the selective pharmacological activation of the ABCC1 transporter significantly reduces the cerebral loading with Aβ and can thus be used therapeutically for the treatment of diseases with disturbed brain proteostasis. Furthermore, the analysis of the transporter activity of the ABCC1 transporter as described above can be used for the indirect or direct diagnosis/prediagnosis of a corresponding disease. Direct analysis would be possible via the administration of substances which are transported via the ABCC1 transporter, and the determination thereof. The indirect analysis has already been described further above.

Changes to export mechanisms which are related to ABC transporters can substantially influence the temporal aggregation profile of Aβ and other brain proteins. Consequently an influencing of the function of the ABCC1 transporter has a positive effect on the risk of developing neurodegenerative diseases, particularly Alzheimer's disease. "Treatment of neurodegenerative diseases" in this sense comprises the prevention and also the treatment of pre-existing diseases.

The role of the ABC transporter in the Aβ release was initially studied in such a manner that it was demonstrated that ABCC1 is able to transport Aβ. For this purpose in vitro transwell assays with endothelial cells (endothelialcelltranswellassay, ECTA) of primary cultivated capillary endothelial cells from mouse brains (cell culture approach) were used.

Primary cultures of endothelial cells from brain capillaries of ABCB1-deficient, ABCC1-deficient (knock out) mice and control mice (C57Bl/6, FVB/N) were used to study the Aβ-specific transport activity. The transport of Aβ from the abluminal (brain) into the luminal (blood) compartment is impaired in ABCB1-deficient and ABCC1-deficient endothelial cells. The mean Aβ transport rate during the first six hours after administration of Aβ peptides (Aβ42) was 2.2 pg/min for the control cells. In contrast to this, the ABCC1-deficient cells only reached half the transport capacity (1.0 pg/min). In the ABCB1-deficient cells the Aβ transport was almost non-existent (0.3 pg/min). Further investigations of capillary endothelial cells and cells from the plexus choroideus revealed that the ABCB1 transporter is strongly expressed in brain capillary endothelial cells whereas the endothelial ABCC1 expression in brain capillaries is lower.

The relative significance of members of the ABC transporter family was then investigated in vivo using newly generated ABC transporter-deficient Alzheimer mouse models. The genetically modified mice each exhibit a deficiency (knock out) at specific ABC transporters ABCG2, ABCB1 or ABCC1.

The Aβ immunohistochemistry of brain sections showed:
i) significant increases in the cortical number and the size of Aβ-positive plaques in ABCC1-deficient mice compared to control mice (see FIGS. 1 and 2a-c).
ii) ABCB1-deficient mice showed a smaller increase in the number and size of Aβ-plaques than ABCC1-deficient mice.
iii) No significant difference could be determined between control mice and ABCG2-deficient mice (FIG. 2a-c).

In order to determine the quantity of buffer-soluble Aβ (mostly monomers and smaller oligomers) and of guanidine-soluble Aβ (mostly fibrillar or aggregated material), enzyme-coupled immune adsorption tests (enzyme-linkedimmunoabsorbentassays, ELISAs) were used for Aβ.

In agreement with the morphological results from the immunohistochemistry, the ABCC1-deficient mice showed a significant increase in aggregated Aβ compared to the control mice at all measurement time points. The cerebral loading with Aβ was greatest at an age of 25 weeks. At this time point, the Aβ values (Aβ42) were 12 times higher than in the control mice. Buffer-soluble Aβ also increased with age but after 25 weeks, at the time of the highest plaque loading, the values of the soluble Aβ in the ABCC1-deficient group decreased substantially.

Further investigations were carried out which provided further proof for the relationship between the possibly lacking removal by ABCC1 and the aggregation of Aβ

The transport kinetics of ABC transporters depend inter alia on specific protein/peptide characteristics such as the specific charge. The Dutch-type variant of the amyloid precursor protein (Dutch mutant, $APP_{dt}$) which introduces an additional negative charge near the interface of the α-secretase of the APP and thus results in a severe cerebral amyloidangiopathy (CAA) influence the elimination of $Aβ_{dt}$ via the blood-brain barrier. The Western blot analyses of brain capillaries and plexuschoroideus (CP) from control mice showed a strong expression of ABCB1 in cerebral capillary endothelial cells (BC) and of ABCC1 in CP (FIG. 3d). Since ABC transporters play an important role in the elimination of Aβ, it was assumed that ABC-transporter-deficient (at the blood-brain barrier and at the blood plexus choroideus barrier) $APP_{dt}$-transgenic mice exhibit an increased accumulation of $Aβ_{dt}$ in meningeal vessels. The degree of CAA in the ABC-deficient $APP_{dt}$ mice was quantified at the age of 24 months. In agreement with the assumption, at least 51% of the vessels were severely impaired (>75% of the vessel wall loaded with Aβ) in the ABCC1-deficient animals compared to 23% in the controls (FIG. 3c).

On the basis of these results, it was investigated how far the content of soluble Aβ in the brain could be reduced/influenced by active-substance-mediated activation of ABC transporters. Mice with amyloid deposits were treated for 30 days with the anti-emeticthiethylperazine(Torecan®,2-(ethylthio)-10-[3-(4-methylpiperazin-1-yl)propyl]-10H-phenothiazine). 3 mg/kg body weight was administered intramuscularly twice daily. The preventative treatment began before the mice exhibited senile plaques. ELISA measurements of the treated animals showed a reduction in the quantity of Aβ of at least 31% in the treated mice compared to vehicle-treated animals (vehicle=water) (FIG. 3e). The results are reproduced graphically in FIGS. 3a-3e.

The capacity to remove Aβ proved to be a key factor in the regulation of the intracerebral accumulation of Aβ.

Thiethylperazine (Torecan®) proved to be a particularly efficient activator of the ABCC1 transporter. Other derivatives starting from the same scaffold also showed good results in the activation of the ABCC1 transporter. The corresponding derivatives are represented in the general formula I

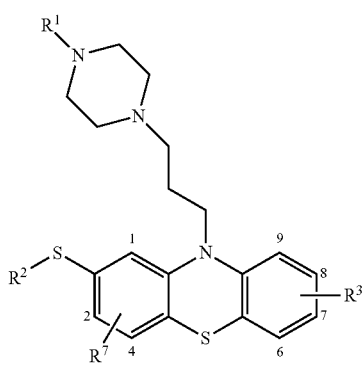

I wherein the residues $R^1$ and $R^2$ are the same or different and each independently of one another are $C_1$-$C_6$ alkyl groups, which independently of one another optionally comprise another substituent selected from alkyl, aryl, acyl (preferably acetyl), amino, nitro, sulfonyl, hydroxyl, alkoxy, aryloxy, arylthio, alkylthio groups and halogen atoms, wherein the respective alkyl groups optionally comprise at least one further halogen atom and the residue $R^3$ is located at one of the positions 6-9 of the phenothiazine ring system and is a hydrogen atom or an alkyl, aryl, acyl (preferably acetyl), amino, nitro, sulfonyl, hydroxyl, alkoxy, aryloxy, arylthio, alkylthio group or a halogen atom, wherein the respective alkyl groups optionally comprise at least one further halogen atom or an $NR^4R^5$ or $OR^6$ group, wherein $R^4$, $R^5$ and $R^6$ are the same or different and each independently of one another are selected from hydrogen and $C_1$-$C_3$ alkyl groups and the residue $R^7$ is located at one of the positions 1, 2 or 4 of the phenothiazine ring system and is a hydrogen atom or an alkyl, aryl, acyl (preferably acetyl), amino, nitro, sulfonyl, hydroxyl, alkoxy, aryloxy, arylthio, alkylthio group or a halogen atom, wherein the respective alkyl groups optionally comprise at least one further halogen atom or an $NR^8R^9$ or $OR^{10}$ group, wherein $R^8$, $R^9$ and $R^{13}$ are the same or different and each independently of one another are selected from hydrogen and $C_1$-$C_3$ alkyl group.

These derivatives are accordingly well suited to the treatment of neurodegenerative diseases, in particular β-amyloidopathies or α-synucleinopathies where the treatment, as already mentioned, comprises both the prevention and the treatment of pre-existing diseases. The halogen atom/the halogen atoms are preferably selected from fluorine and chlorine. The acyl groups (—(C=O)-R) of the residues $R^{1,2,3,7}$ are preferably acetyl groups (—C(=O)CH$_3$). preferably the residues $R^1$ and $R^2$ are the same or different and each independently of one another are a $C_1$-$C_6$ alkyl group or a $C_1$-$C_6$ alkyl group (preferably $C_1$ alkyl) substituted with an acetyl group and the residues $R^3$ and $R^7$ are hydrogen or an acetyl group. In a preferred embodiment the residues $R^1$ and $R^2$ are the same or different and each independently of one another are a $C_1$-$C_3$ alkyl group. It is further preferred that the residues $R^3$ and $R^7$ are hydrogen. It is particularly preferred that the residue $R^1$ is a methyl group, the residue $R^2$ is an ethyl group and the residues $R^3$ and $R^7$ are hydrogen (thiethylperazine, Torecan®). When used for the treatment of neurodegenerative diseases, it has proved advantageous to add further active substances, preferably 1-benzohydrylpiperazines, most preferably 1-benzohydryl-4-cinnamyl piperazine (cinnarizine).

Various neurodegenerative diseases can be treated with the 2-($R^2$-thio)-10-[3-(4-$R^1$-piperazin-1-yl)propyl]-10H-phenothiazine derivatives according to the invention or can be diagnosed by means of the indirect analysis described above. In a particularly preferred embodiment, the neurodegenerative disease is a β-amyloidopathy, in particular Alzheimer's dementia (AD). Another embodiment relates to the case that the neurodegenerative disease is an α-synucleinopathy, in particular Parkinson's disease (PD). Both diseases, i.e. β-amyloidopathy and α-synucleinopathies are characterized by cerebral protein deposits which can be treated by means of an activation of the ABCC1 transporter or can be diagnosed by means of its activity.

Other diseases which can also be treated by activation of the ABCC1 transporter or which can be diagnosed by means of the ABCC1 transporter activity are mentioned hereinafter. Another treatable disease is thus Lewy body dementia (LBD). This is also characterized by cerebral protein aggregation, i.e. is a β-synucleinopathy like Parkinson's disease.

Another embodiment relates to the case that the neurodegenerative disease is Huntington's disease (HD). Another embodiment relates to the case that the neurodegenerative disease is a prion disease, in particular Creutzfeld-Jacob disease (CJD) orfatalfamilialinsomnia (FFI). Another embodiment relates to the case that the neurodegenerative disease is a tauopathy, in particular cortico-basal degeneration (CBD), Steel-Richardson-Olszewski syndrome (PSP, progressivesupranuclearpalsy) or Pick's disease (Pi D). Another embodiment relates to the case that the neurodegenerative disease frontotemporaldegeneration (FTLD), in particular ubiquitin-positive degeneration, TDP43-positive degeneration or forubiquitin and TDP43-negative degenerations. Another embodiment relates to the case that the neurodegenerative disease is an amyotrophiclateralsclerosis (ALS). Another embodiment relates to the case that the neurodegenerative disease is a spinocerebellarataxia (SCA) or spasticparaparesis (SPG). Another embodiment relates to the case that the neurodegenerative/neuroimmunological disease ismultiple sclerosis (MS) or an MS-related syndrome, in particular ADEM or Devic's syndrome.

DESCRIPTION OF THE FIGURES

In the figures

FIG. 3a shows that at an age of 25 weeks ABCC1 deficiency leads to a marked increase (~12 times) in insolubleAβ; and FIG. 3b shows that the quantity of buffer-soluble Aβ42 at an age of 25 weeks is noticeably reduced compared with 22 weeks (−56%). This is probably due to the deposition in insoluble deposits. At the same age the area covered by Aβ deposits which is measured in the immunohistochemistry is increased by 83% (error bars, standard error n≥5, p<0.05);

FIG. 3c shows that 53% of the blood vessels are severely impaired by CAA (>75% of the vessel walls exhibit Aβ). This relates to ABCC1-deficient mice (ABCC1ko) compared to 23% in the controls (n=3);

FIG. 3d shows that the expression of ABCC1 can be seen predominantly in the plexus choroideus (CP) whereas ABCD1 is principally expressed in the capillaries of the brain (BP);

FIG. 3e shows that the activation of ABCC1 by thiethylperazine (Torecan) lowers the Aβ values in mice (−28%), error bars, standard error (n=4, *p<0.05).

EXAMPLES

Animals

Figure 1A:
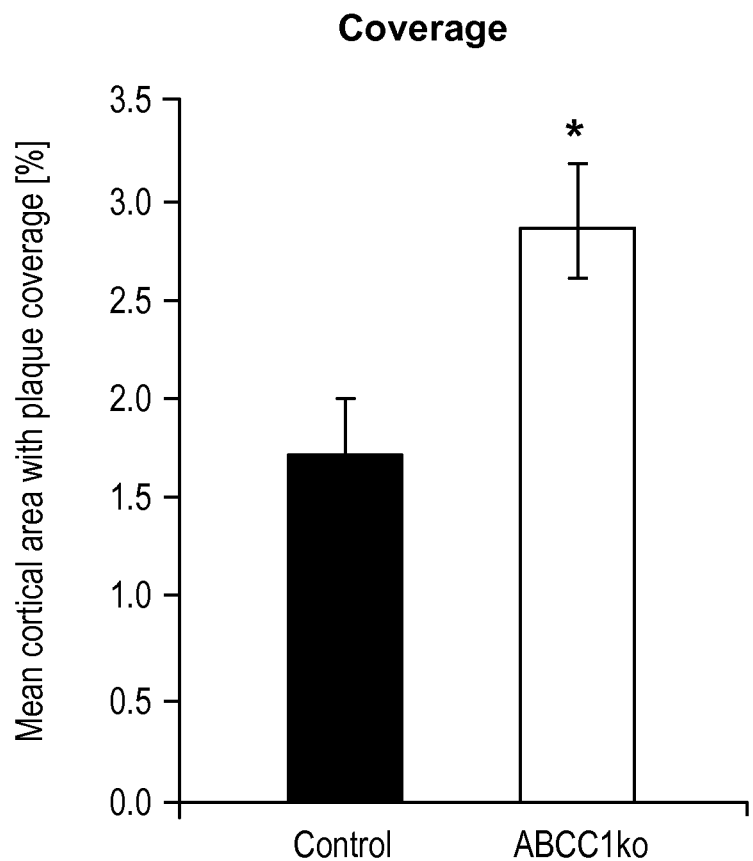
FIG. 1a shows that the cortical density of neuritic plaques in ABCC1-deficient mice (ABCCI ko) is increased by ~75%.
Figure 1B:
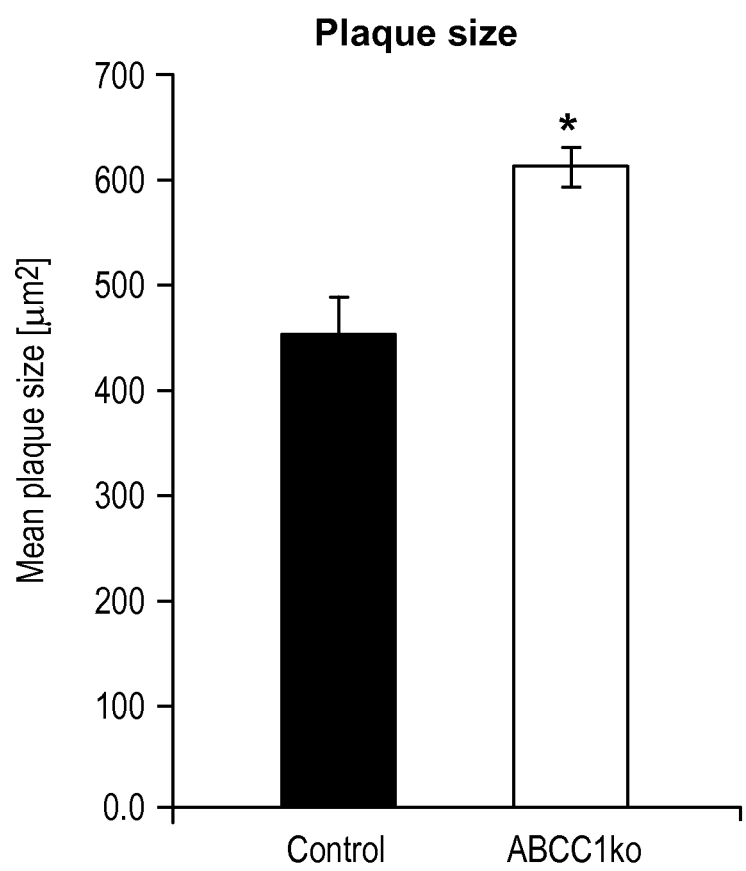
FIG. 1 b,c shows that the mean plaque size is increased (+34%) as a result of the larger number of plaques (+63%) having a size of more than 700 μm$^2$ and a lower frequency of smaller plaques (−24%). Error bars, standard error (n≥3)
FIG. 1d shows that the IHC staining in ABCG2-deficient (ABCG2ko), ABCB1-deficient (ABCBIko), ABCC1-deficient (ABCCIko) miceand in control mice shows a higher surface density of Aβ in ABCC1-deficient animals. Typical plaques of the same size are shown in section, scaling bars represent 500 μm (overview) and 50 μm (section) (*p<0.05)
Figure 1C:
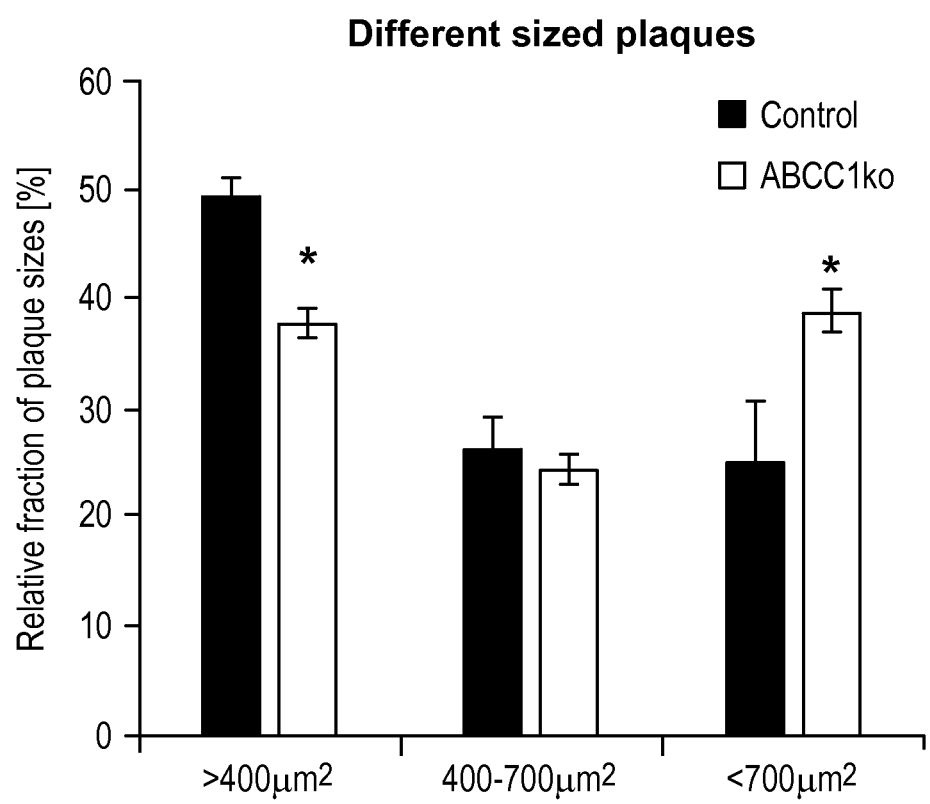
Figure 1D:
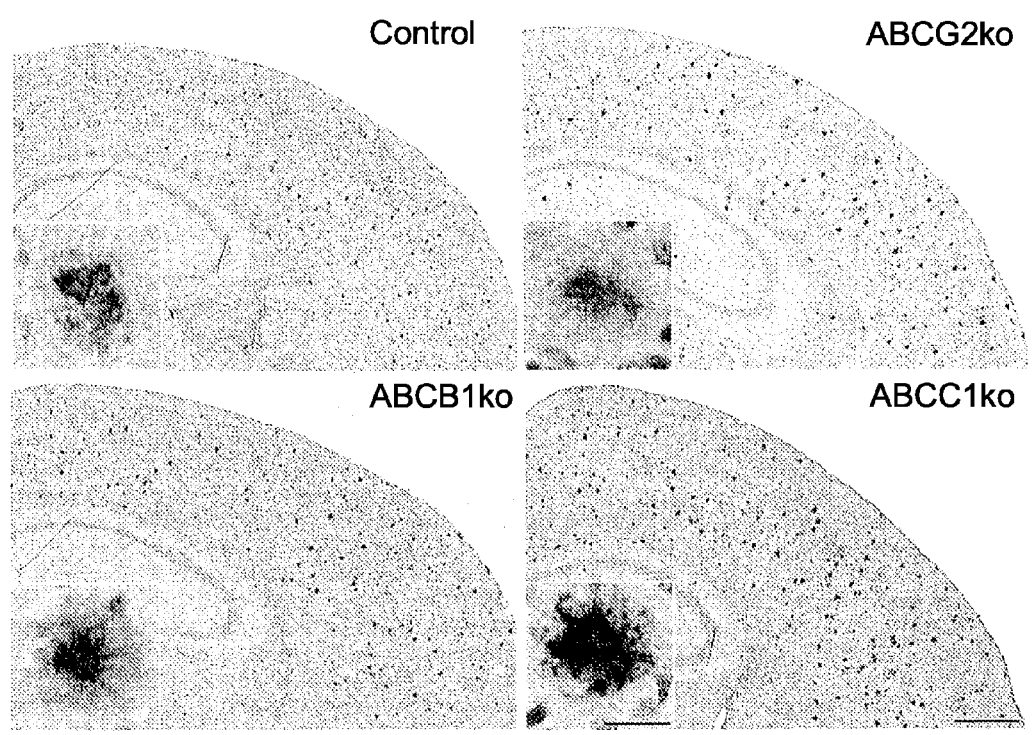
Figure 2A:
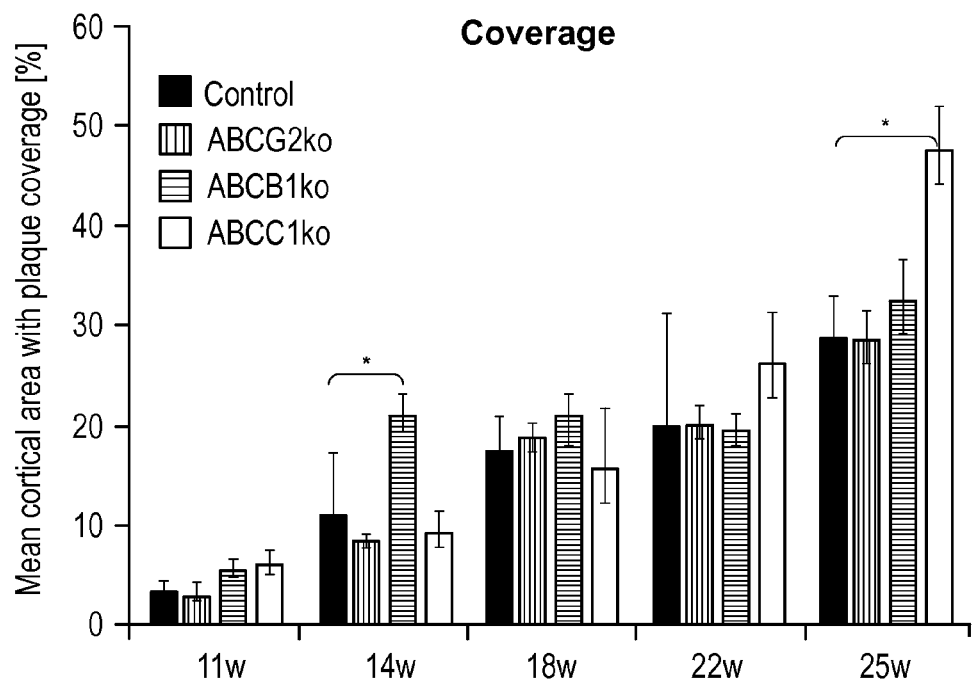
FIG. 2a shows that the plaque density in the cortex (coverage) in specific ABC-transporterknockout mice is increased. In particular ABCC1-deficient (ABCCIko) mice show an increased Aβ-amyloid loading (light-grey bars, in each case on the outside right in the individual groupings), w=week on the abscissa.
Figure 2B:
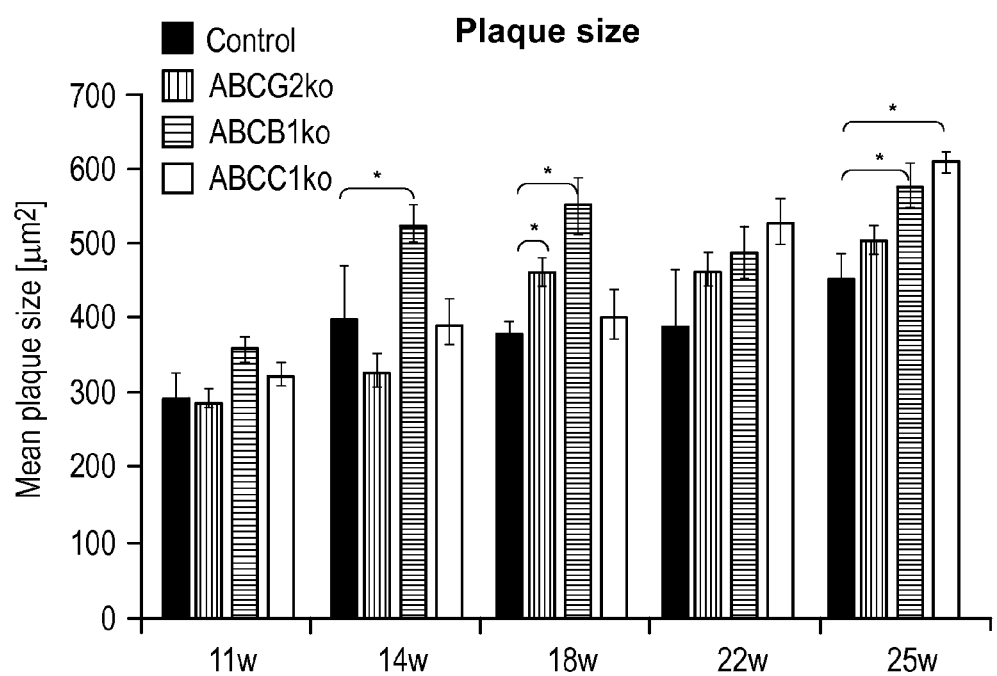
FIG. 2b shows that the total plaque size in ABCC1-deficient (ABCCIko) and ABCB1-deficient (ABCBIko) mice at the age of 25 weeks is increased, w=week on the abscissa.
Figure 2C:
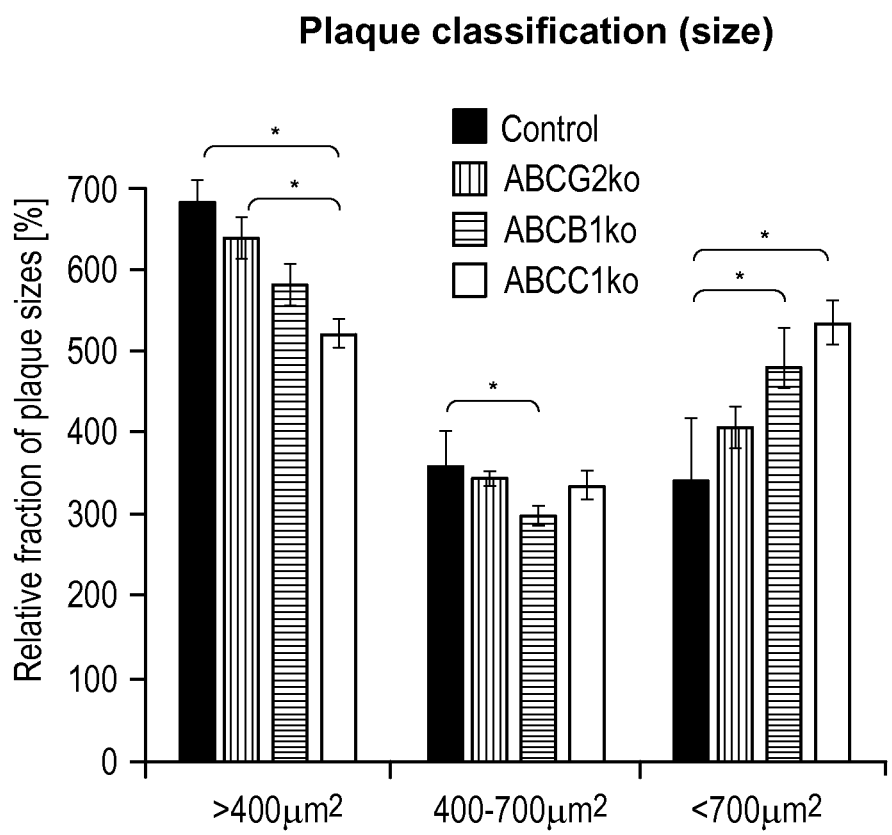
FIG. 2c shows that the total increase in the plaque size is associated with fewer smaller plaques and more larger plaques (>700 μm$^2$) whereas the number of medium-size plaques remains at the same value, error bars, standard error (n≥5), *p<0.05.
Figure 3A:
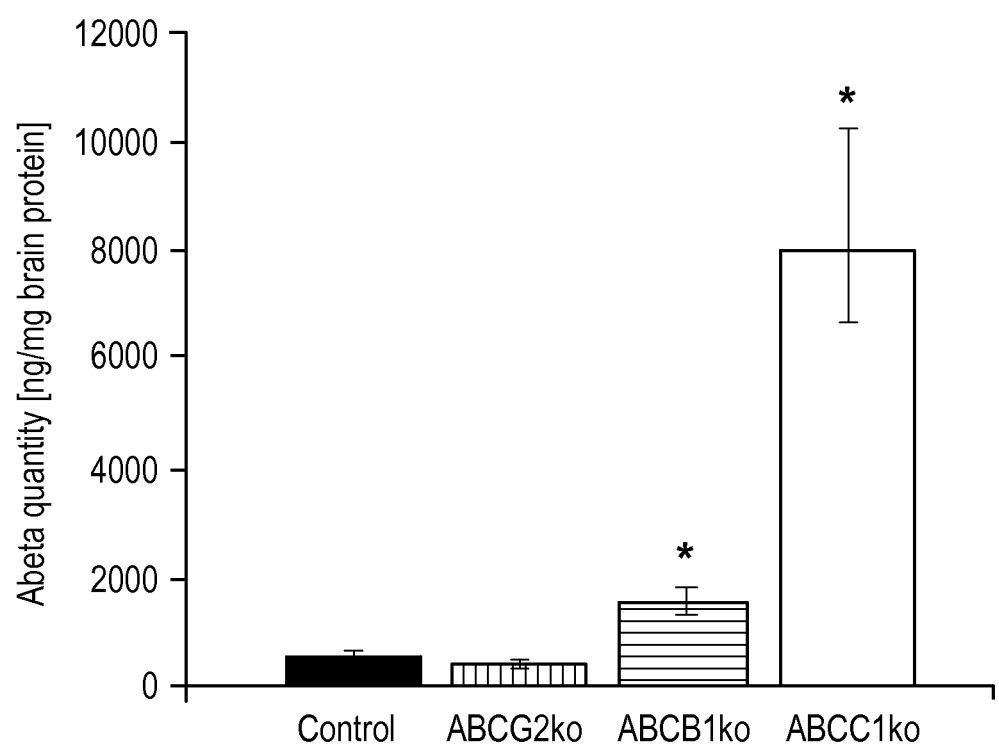
FIGS. 3a-3e show that the deficiency of ABCC1 promotes the accumulation of Aβ and Aβ$_{dt}$ and that the activation of ABCC1 (by administration of Torecan) reduces the Aβ values; where
Figure 3B:
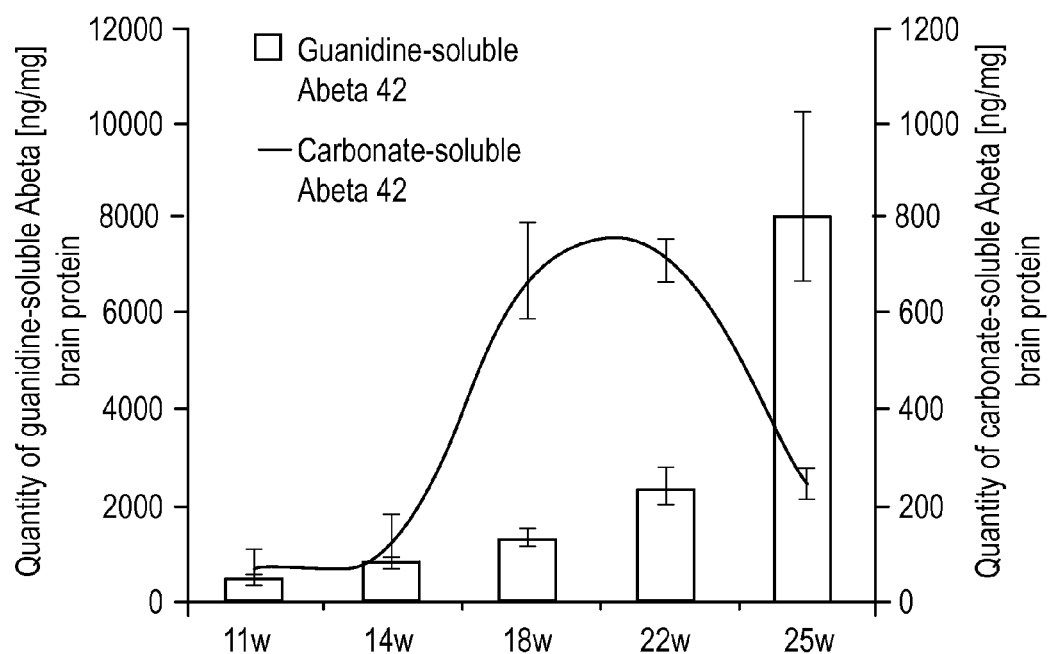
Figure 3C:
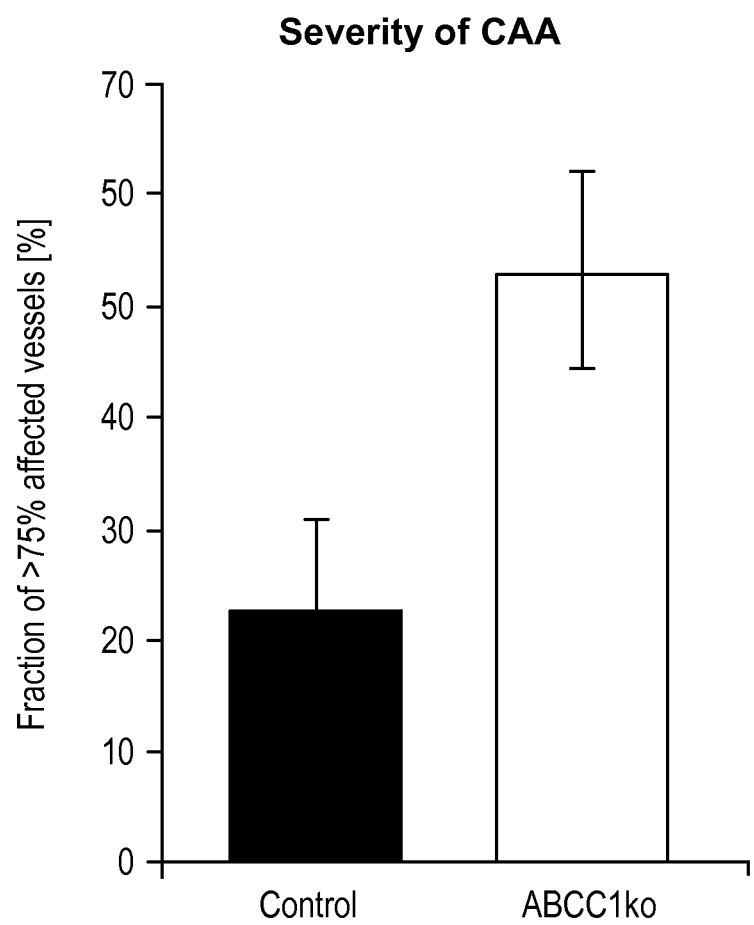
Figure 3D:
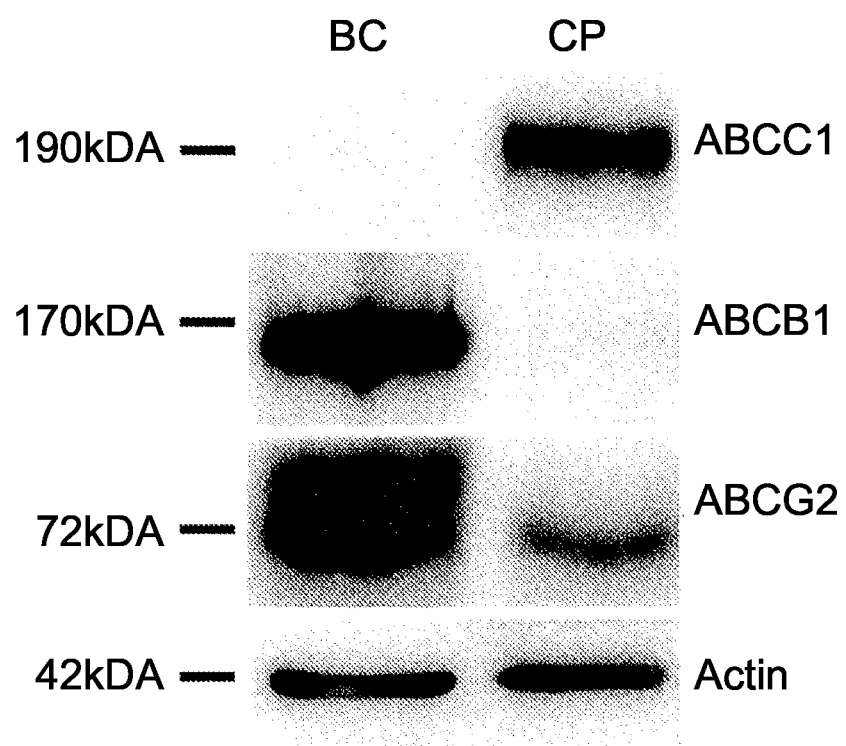
Figure 3E:
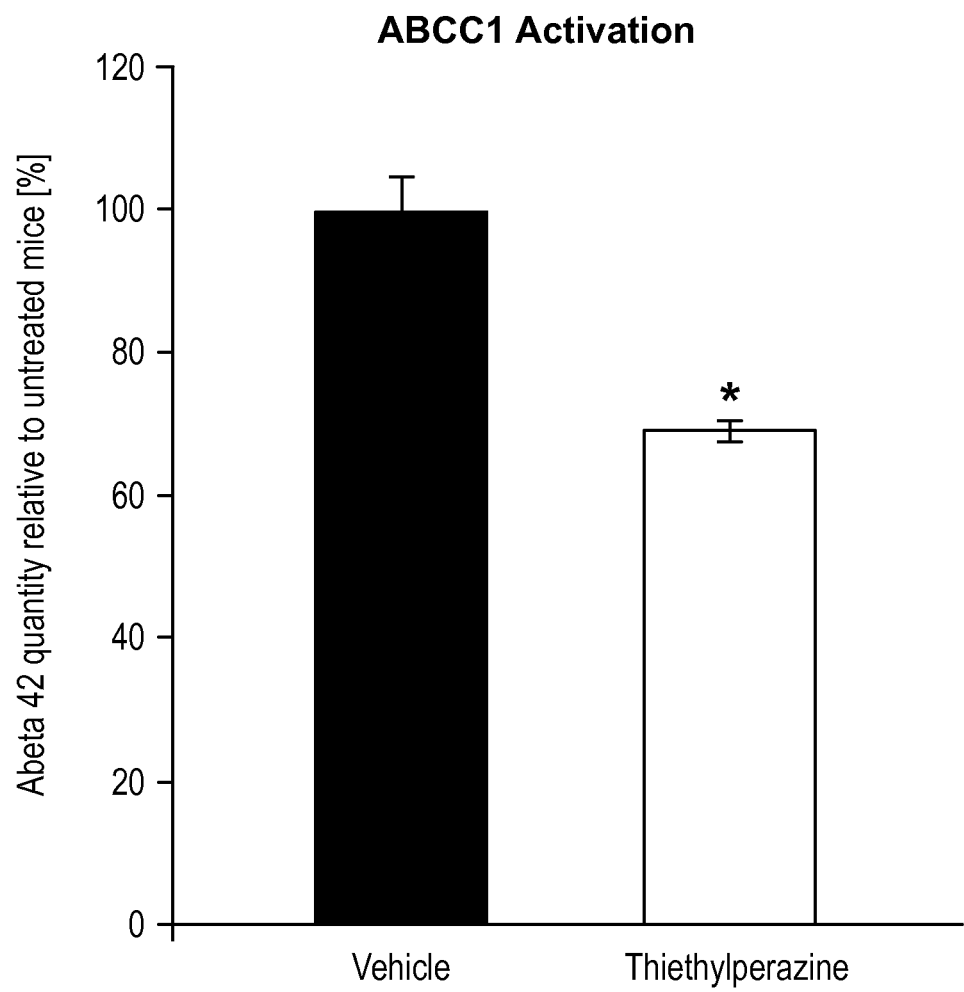

APP-transgenic mice (APP, APP$_{dt}$) were obtained from The Jackson Laboratory (Bar Harbor, USA) and the University of Tübingen (Tübingen, Germany). The NEP-deficient mice were obtained from the Riken Brain Research Institute (Saitama, Japan). ABCG2-, ABCB1-, and ABCC1-deficient mice were obtained from Taconic-Farms (Denmark). All transgenic and knockout mouse lines were hybridised for at least 9 generations in the geneticFVB-background. The mice were held in a 12 h/12 h light/dark cycle at 23° C. with free access to food and water.

Methods
Tissue Preparation

For the tissue preparation the mice were killed by cervical dislocation and perfused transcardially with PBS (phosphate-buffered, physiological saline solution). The brain was removed and one hemisphere was stored in buffered 4% paraformaldehydefor paraffin embedding andimmunohistochemistry. The other hemisphere was shock-frozen in liquid nitrogen and stored at −80° C. for biochemical analyses.
ELISA ELISA kits (TH40HS, TK42HS) from The Genetics Company (TGC, Schlieren, Switzerland) were used for the quantification of Aβ. Brain hemispheres were homogenised using PreCellys24 (12 s, 6,500 rpm). After addingcarbonate buffer (pH 8.0) the homogenisates were mixed using PreCellys (5 s, 5,000 rpm) and centrifuged for 90 min at 4° C. and 24,000 g, in order to separate insoluble from soluble Aβ species. The remaining supernatant (buffer-soluble fraction) was mixed with 8M guanidine hydrochloride in a ratio of 1:1.6. To extract the aggregated Aβ species, the pellet was dissolved in 8 volumes of 5M guanidine hydrochloride, agitated at room temperature for 3 h and centrifuged at 24,000 g for 20 min at 4° C. The remaining supernatant formed the guanidine-soluble fraction (GuaHCl). Protein contents of all the samples were measured three times, using a Nanodrop1000 spectrophotometer (ThermoFisher Scientific, Wilmington, USA). The ELISAswere carried out according to the manufacturer's instructions using suitable dilutions.
Western Blots Tissue homogenisates were prepared for the Western Blots. The total protein concentrations of the extracts were determined using a BCA assay (Pierce, part of Thermo Fisher Scientific, Rockford, USA). After electrophoresis of 10 μg total protein per trace, the proteins were blotted onto PVDF membranes. After blocking in 5% dry milk in TBST-buffer (50 mMTris pH 7.4, 150 mMNaCl, 0.1% Tween20) for 1 h at room temperature, the blots were studied either on ABCB1 (1:500, D-11, Santa Cruz), ABCC1 (1:200, Alexis Bio) or β-actin (1:20.000, Sigma) overnight at 4° C. Anti-mouse-HRP, anti-rat-HRP oranti-hare-HRP were used as detection antibodies. An Amersham ECL Plus Detectionkitand a RoperCoolSnap HQ² camera were used for visualisation.

Immunohistochemistry (IHC)

Formalin-fixed brains were embedded in paraffin and cut into 4 μm thick sections. After removing the paraffin, the sections were further treated with a BondMax™ Autostainer (Menarini/Leica, Germany). Immunostaining was initiated after blocking of endogenic peroxidase (5 min) and epitoperetrieval for 5 min using 95% formic acid (for antibody 6F3D, Dako, Germany) and 70% formic acid (for antibody 4G8, Millipore, Germany). Primary antibodies were routinely incubated at room temperature for 30 min with the following dilutions: 6F3D (1:100), 4G8 (1:500). Primary antibodies were detected with theBondMax™ Bond Polymer Refinedetectionkit and according to the DAB R30 standard protocol. The sections were completely digitised with a resolution of 230 nm using a MiraxDesk/MiraxMidi scanner and then analysed automatically using the AxioVision software package (Zeiss, Germany).

Assessment of the Severity of the CAA

Brain sections of $APP_{dt}$ were stained with 4G8-antibody. At least two non-consecutive sections were studied for CAA of the meningeal vessels in a masked manner. All meningeal vessels were counted manually and the severity of the CAA was categorised as follows:

Category I: not adversely affected
Category II: ≤25% of the periphery positively stained
Category III: ≤50% of the periphery positively stained
Category IV: ≤75% of the periphery positively stained
Category V: ≤00% of the periphery positively stained The average number of vessels for each category was calculated relative to the total number of identified vessels.

Endothelial Cell Transwell Assay (ECTA)

Endothelial cells of mouse brain capillaries were prepared as described in Coisne et al. (Coisne, C. et al. Mouse syngenic in vitro blood-brain barrier model: a new tool to examine inflammatory events in cerebral endothelium. Laboratory Investigation; 85, 734-746 (2005)). At least 3-4 week old mice were beheaded and the brains removed. Following dissection of the brain stem, the white matter and the meninges, the tissue was homogenised in two volumes of wash buffer B (WBB) (Hanks bufferedsaltsolution (HBBS), 10 mM HEPES, 0.1% BSA) using a 15 ml glassdouncer (Wheaton Industries, Millville, N.J.; USA). One volume of 30% dextran solution was added to the homogenisate. This was centrifuged twice at 3,000 g and 4° C. The pellet containing the vessels was resuspended in WBB and large vessels were broken up manually by harsh pipetting of the solution. Vacuum filtration through 60 urn membranes (SEFAR, Switzerland) was used to separate large vessels from the capillaries. After combined treatment with collagenase/dispase (HBSS, 10 mM HEPES, 0.15 g/ml TCLK, 10 μg/ml DNAse-I, 1 mg/ml collagenase/dispase (Roche) single cell suspension was achieved by further harsh pipetting of the solution. Endothelial cells wereinserted intoMatrigel-coatedTranswellinserts (0.4 μmpores, Greiner Bio-One, Germany) having a density of 120,000 cells per insert and allowed to grow on a supporting glial culture.

Sulphur yellow was used to determine the paracellular flux during the assay. The culture medium of the abluminal compartment was replaced with a solution containing 10 ng Ass42 (1.6 nM final concentration). Samples from the luminal compartment were then taken after 2 h, 6 h or 24 h and the Aβ content was determined with ELISA (TK42-highsense, TGC, Switzerland). The transport rate was described in Coisne et al. (Coisne, C. et al. Mouse syngenic in vitro blood-brain barrier model: a new tool to examine inflammatory events in cerebral endothelium. Laboratory Investigation; 85, 734-746 (2005)).

ELISA Statistics

TheLillieforsgoodness-of-fit test (alpha=0.05) was applied to the ELISA data and to the log-transformed ELISA data to distinguish between the assumption of normally distributed sample data and the assumption of log-normally distributed sample data. Despite the small sample size, the null hypothesis ($H_0$) was dismissed for both sets of data for 5 of 44 samples. In agreement with the observation of predominantly positive (skew) and strictly positive sample data, the assumption of normally distributed data was rejected. Mean confidence intervals were calculated assuming a basic log-normal distribution. The Wilcoxon rank-sum test was applied to compare the ELISA data of the various mouse strains for each time point.

The invention claimed is:

1. A method for the diagnosis or prediagnosis of a β-amyloidopathy or α-synucleopathy accompanied by a cerebral protein deposit and a reduced activity of the cerebral ABCC1-transporter, or for determining the risk of a proband to develop such an illness, wherein the proband has been administered at least one substance transported by the cerebral ABCC1 transporter, comprising the following steps:
   a) determining a quantity of ingested substance in at least one body fluid sample of the proband at a specific time point;
   b) repeating the determining step a) at at least one later time point; and,
   c) comparing the quantities determined in steps a) and b) with quantities which had been defined as characteristic at the same time points for probands that showed no clinical symptoms of a β-amyloidopathy or an α-synucleopathy in order to determine activity of the cerebral ABCC1 transporter.

2. The method of claim 1, wherein the body fluid samples of the proband are samples of at least one of blood plasma, blood serum, and cerebrospinal fluid.

3. The method of to claim 1, wherein the β-amyloidopathy is an Alzheimer's dementia.

4. The method of claim 1, wherein the α-synucleopathy is Parkinson's disease or Lewy body dementia.

5. The method of claim 1, wherein the substances transported via the cerebral ABCC1 transporter are selected from the group consisting of antibiotics, virostatics/antiviral medicaments, anti-allergics/antihistamines, cardio-vascular medicaments, antidepressants, antihyperuricemics, cytostatics, vitamins/vitamin analogues, antiphlogistics, anti-epileptics, hormones/hormone derivatives, leukotrienes, fluorescent samples, GSH-, sulfate or glucoronide-coupled metabolites of endogenous natural substances, toxins, and medicaments.

* * * * *